US009142045B1

(12) United States Patent
 Cavanaugh (10) Patent No.: US 9,142,045 B1
(45) Date of Patent: Sep. 22, 2015

(54) METHOD FOR DISPLAYING TWO-DIMENSIONAL GEOLOGICAL IMAGE DATA IN LOG FORMAT AND DISPLAYED PRODUCT

(71) Applicant: Ingrain, Inc., Houston, TX (US)

(72) Inventor: Timothy Cavanaugh, Houston, TX (US)

(73) Assignee: InGrain, Inc., Houston, TX (US)

( * ) Notice: Subject to any disclaimer, the term of this patent is extended or adjusted under 35 U.S.C. 154(b) by 168 days.

(21) Appl. No.: 13/649,198

(22) Filed: Oct. 11, 2012

Related U.S. Application Data

(60) Provisional application No. 61/547,095, filed on Oct. 14, 2011.

(51) Int. Cl.
 *G06T 11/20* (2006.01)
 *G06T 11/00* (2006.01)

(52) U.S. Cl.
 CPC ............... *G06T 11/206* (2013.01); *G06T 11/00* (2013.01); *G06T 11/20* (2013.01)

(58) Field of Classification Search
 None
 See application file for complete search history.

(56) References Cited

U.S. PATENT DOCUMENTS

| 6,855,936 | B2 | 2/2005 | Yamamoto |
| 7,750,293 | B2 | 7/2010 | Principe |
| 8,725,477 | B2 * | 5/2014 | Zhang et al. .................... 703/10 |
| 2009/0259446 | A1 * | 10/2009 | Zhang et al. ..................... 703/2 |
| 2011/0004447 | A1 * | 1/2011 | Hurley et al. ..................... 703/1 |
| 2012/0113242 | A1 * | 5/2012 | Crandall et al. ................ 348/79 |

OTHER PUBLICATIONS

Croudace et al., "ITRAX: description and evaluation of a new multi-function X-ray core scanner", Geological Society, London, Special Publications, 2006, p. 51-63.*
Knackstedt et al., "Digital Core Laboratory: Properties of reservoir core derived from 3D images", Society of Petroleum Engineers, Inc., 2004.*
Lewis et al., "New Evaluation Techniques for Gas Shale Reservoirs", Schlumberger, 2004.*
Tomutsa et al., "Focussed Ion Beam Assisted Three-Dimensional Rock Imaging at Submicron Scale", Berkeley Lab, 2003.*

* cited by examiner

*Primary Examiner* — Phi Hoang
*Assistant Examiner* — Diane Wills
(74) *Attorney, Agent, or Firm* — Kilyk & Bowersox, P.L.L.C.

(57) ABSTRACT

The present invention relates to a method for displaying two-dimensional geological image data in log format and the displayed image products thereof. The present invention can provide a concatenated display format for two-dimensional image data captured for different planar slices of a geological sample. The present method provides an enhanced format modality for presentation of such image data of a geological sample as a continuous presentation for the slices in the sequence.

17 Claims, 5 Drawing Sheets

METHOD FOR DISPLAYING TWO-DIMENSIONAL GEOLOGICAL IMAGE DATA IN LOG FORMAT AND DISPLAYED PRODUCT

This application claims the benefit under 35 U.S.C. §119 (e) of prior U.S. Provisional Patent Application No. 61/547,095, filed Oct. 14, 2011, which is incorporated in its entirety by reference herein.

BACKGROUND OF THE INVENTION

The present invention relates to a method for displaying two-dimensional geological image data in log format and the displayed image products thereof.

In the field of digital rock physics, devices for generating computer tomographic (CT) images of rock samples, such as drill cuttings, have become available and used to analyze the rock samples. Such CT image generating devices have been used to produce two-dimensional (2D) gray scale images of the rock samples. The two-dimensional images are individually displayable. The two-dimensional images also can be stacked into a three-dimensional volume for which selected image slices can be displayed. Such gray scale images have been used, for example, as part of an analysis to obtain estimates of petrophysical parameters of the imaged rock sample, for example, porosity, permeability, shear and bulk moduli, and formation resistivity factor.

The present investigators have recognized that it would be beneficial to provide a new technique for displaying image data captured for different planar slices of a geological sample as a more continuous or semi-continuous presentation which can include or embed geological phase data associated with each image and include more information on the context and reservoir orientation of the samples from which the images are derived.

SUMMARY OF THE INVENTION

A feature of the present invention is to provide a method for displaying two-dimensional geological image data as two-dimensional images obtained at different depths within the sample in a log format.

Another feature of the present invention is to provide a method of concatenating two-dimensional geological image data obtained at different planar slices of a geological sample in a log format.

An additional feature of the present invention is to provide displayed imaged products of the indicated methods.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a method for generating a method of displaying geological image data, wherein the method comprises a step (a) of capturing a plurality of two-dimensional images of slices of a geological sample in a sequence, the plurality of two-dimensional images comprising a first dimensional direction and a second dimensional direction perpendicular to the first dimensional direction, wherein locations of at least one geological phase of the geological sample are captured. In a step (b), a determination is made if any of the plurality of two-dimensional images in the sequence are to be replaced with a replacement gap when joined. In a step (c), the plurality of two-dimensional images and any gaps are joined in the sequence to form a continuous stitched image. In a step (d), proportional magnitudes of at least one geological phase are calculated based on the total geological phases for each of a plurality of adjoining rows of pixels in the stitched image, wherein the plurality of adjoining rows of pixels in the stitched image each extend from corresponding adjacent first positions along the first dimensional direction of the sequential slices in a direction parallel to the second dimensional direction of the sequential slices. In a step (e), the proportional magnitudes calculated for the at least one of geological phase are plotted for each of the plurality of adjoining rows of pixels in the stitched image at corresponding first adjacent locations on a first portion of a two-dimensional graph. The two-dimensional graph comprises a first axis extending in a same direction as the first dimensional direction and a second axis extending in a same direction as the second dimensional direction. The first adjacent locations on the first portion of the two-dimensional graph each comprise a first axis coordinate corresponding to the position of each row of the pixels and a second axis coordinate corresponding to the proportional magnitude for the corresponding row of pixels. As an option, the method can further comprise displaying the two-dimensional graph parallel and adjacent to the captured images, wherein the plotting further comprising plotting of the proportional magnitudes adjacent the corresponding captured two-dimensional images in the stitched image.

The present invention further relates in part to a method of displaying geological image data, wherein the method comprises capturing a plurality of two-dimensional SEM images of sequential slices of a geological sample in a direction from a surface toward an interior of the geological sample, the plurality of two-dimensional images comprising a first dimensional direction and a second dimensional direction perpendicular to the first dimensional direction, wherein locations of at least one geological phase of the geological sample are captured. A determination is made if any of the plurality of two-dimensional images are to be replaced with a replacement gap when joined. Then, the plurality of two-dimensional SEM images and any gaps are joined in sequence in a common plane with an image of a deeper slice joined below the image of an adjacent shallower slice to form a vertically stitched image having a vertical dimension and a horizontal dimension. A plurality of proportional magnitudes of a first geological phase are calculated based on the total geological phases for each of a plurality of adjoining rows of pixels in the vertically stitched image. The plurality of adjoining rows of pixels in the vertically stitched image each extend from corresponding adjacent first positions along the first dimensional direction of the sequential slices in a direction parallel to the second dimensional direction of the sequential slices. The plurality of proportional magnitudes of the first geological phase are plotted for each of the plurality of adjoining rows of pixels of the first image at corresponding first adjacent locations on a first portion of a two-dimensional graph, wherein the two-dimensional graph comprises a first axis extending in a same direction as the first dimensional direction and a second axis extending in a same direction as the second dimensional direction. The first adjacent locations on the first portion of the two-dimensional graph each comprise a first axis coordinate corresponding to the plurality of rows of adjacent pixels and a second axis coordinate corresponding to the plurality of proportional magnitudes.

The present invention further relates in part to a graphical display of geological image data which comprises a vertically stitched image and a two-dimensional graph. The vertically stitched image has a plurality of images of sequential planar slices of a geological sample joined in a plane with each image of a deeper slice joined below the image of an adjacent shallower slice. The vertically stitched image has a vertical direction and a horizontal direction. The two-dimensional graph comprises a first axis and a second axis, and a plurality of proportional magnitudes of at least one geological phase based on the total geological phases in the geological sample calculated from a plurality of adjoining vertical rows of pixels in the vertically stitched images. The plurality of adjoining rows of pixels in the vertically stitched images each extend from corresponding adjacent first positions along the vertical direction of the first planar slice in a direction parallel to the horizontal direction of the first planar slice. The plurality of proportional magnitudes are located at coordinates corresponding to respective positions on the first axis and calculated positions on the second axis corresponding to the plurality of proportional magnitudes. The vertically stitched image is displayed parallel to the graphed plurality of proportional magnitudes, such that a row pixels of the stitched image from which the plurality of proportional magnitudes is calculated lines up respectively with the plots of the plurality of proportional magnitudes on the graph. As an option, the graphical display can further comprise the two-dimensional graph displayed parallel and adjacent to the captured images.

As used herein, "stitching" refers to combining a plurality of two-dimensional image files into a single file. As part of the combination into a single file, two-dimensional images of the files can be arranged as a non-overlapping concatenation of successive images to provide a continuous image without gaps or with gaps between any two different images used in forming the continuous image. The arrangement of successive images in this manner may be generally referred to herein as "stitched" with the understanding that it is not required that the successive images be arranged in a completely seamless transition from one to the other, although that can be done in an example of the present application.

As used herein, a "log format" refers to a concatenating of a plurality of portions of image data derived from different slices of a geological sample with stitching to form a continuous image, which portions of the continuous image can be segmented and plottable material results can be calculated for individual rows of pixels thereof, and the continuous image, these plottable calculated material results, or both can be displayed, printed out, or both, in a log form of presentation.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate some of the embodiments of the present invention and together with the description, serve to explain the principles of the present invention. The drawings are not necessarily drawn to scale. Like numerals in the drawings refer to like elements in the various views.

DETAILED DESCRIPTION OF THE PRESENT INVENTION

The present invention relates in part to a method for providing a unique two-dimensional display in log format of image data captured on different planar slices of a geological sample. The present invention can provide a concatenated or stitched display format for two-dimensional image data captured for different planar slices of a geological sample. The present method provides an enhanced format modality for presentation of such image data of a geological sample as a continuous presentation for the slices in the sequence. As an option, a plurality of images, for example, pixelated grayscalable images, can be captured for different planar slices at different depths through a geological sample, and then image data for more than one of the images can be stitched together in their sequence of acquisition to form a stitched image. The stitched image can be segmented and then materials or phases present in each row of pixels can be calculated and plotted to create a continuous or semi-continuous presentation of the image data in a log format. This log format of the present invention can facilitate an analyst's interpretation of 2D images captured on a given geological sample by providing more context and reservoir orientation to the viewer for the images being displayed together. As an option, the present method provides a technique for displaying two-dimensional image data captured for different planar slices of a geological sample which displays can include or embed geological phase data associated with each image and include more information on the context and in-ground orientation of the samples from which the images are derived. As an option, the concatenating together of the image portions associated with different planar slices of the geological sample can be performed digitally. The stitched image product of the method can be displayed, printed, or both in the log format. As an option, the stitched image portions in the graphical displays or printed products of the present invention permit the data to be conveniently and readily reviewed by merely scrolling up or down the display or printout.

Figure 1:
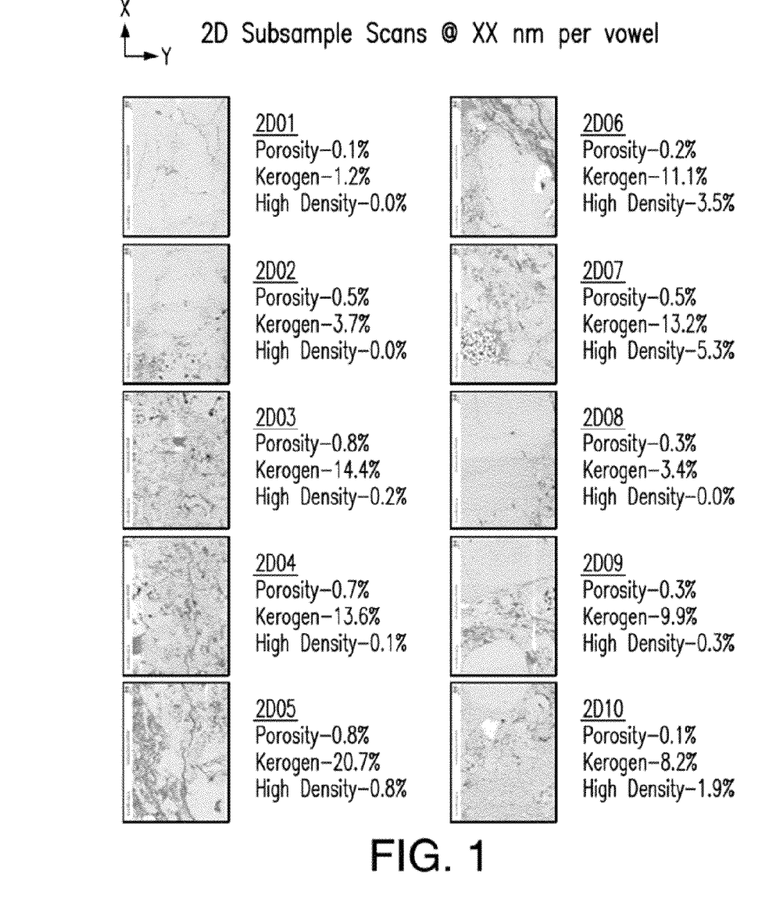
FIG. 1 shows a series of ten (10) two-dimensional (2D) images, denoted as images 2D01 to 2D10, captured via SEM scans at different slices of a rock sample.
Figure 2:
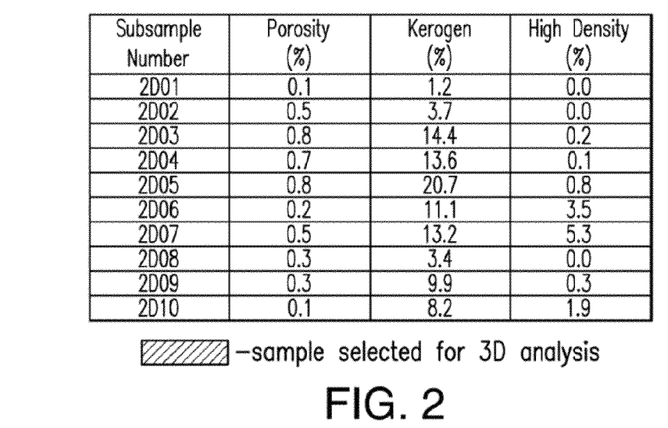
FIG. 2 is a table showing the porosity (%), kerogen (%), and high density mineral (%) content in each of images indicated in FIG. 1.
Figure 3:
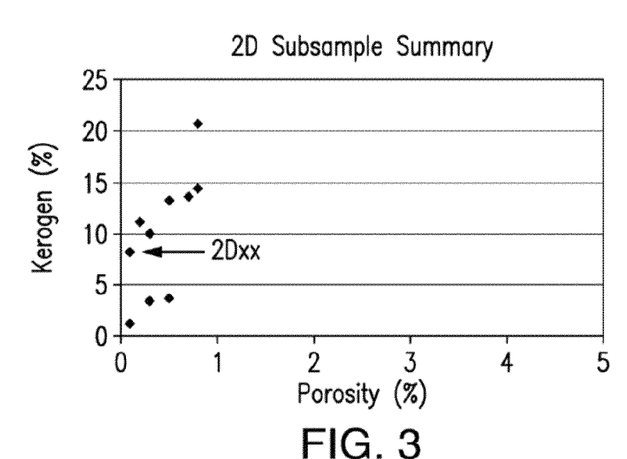
FIG. 3 is a scatterplot of the porosity (%) and kerogen (%) of the images indicated in FIG. 1 and FIG. 2.

The present invention can avoid problems with presenting results for each two-dimensional image individually. For comparison in this respect, FIG. 1 shows a series of ten (10)

two-dimensional (2D) images, denoted as images 2D01 to 2D10, captured via SEM scans at different slices of a rock sample. The rock sample was a shale rock. FIG. 2 is a table showing the porosity (%), kerogen (%), and high density mineral (%) content in each of images indicated in FIG. 1. These 2D SEM results in isolation can be difficult to interpret. Context and reservoir orientation of the individual images with respect to each other and the geological sample can be unclear. Presenting each image individually can also lead to skewed data. For example, if an image happens to contain one large grain or a significant fracture system, the results are still plotted as a single data point for that image. FIG. 3 is a scatterplot of the porosity (%) and kerogen (%) of the images indicated in FIG. 1 and FIG. 2. The data is difficult to interpret when presented in this format.

Figure 4:
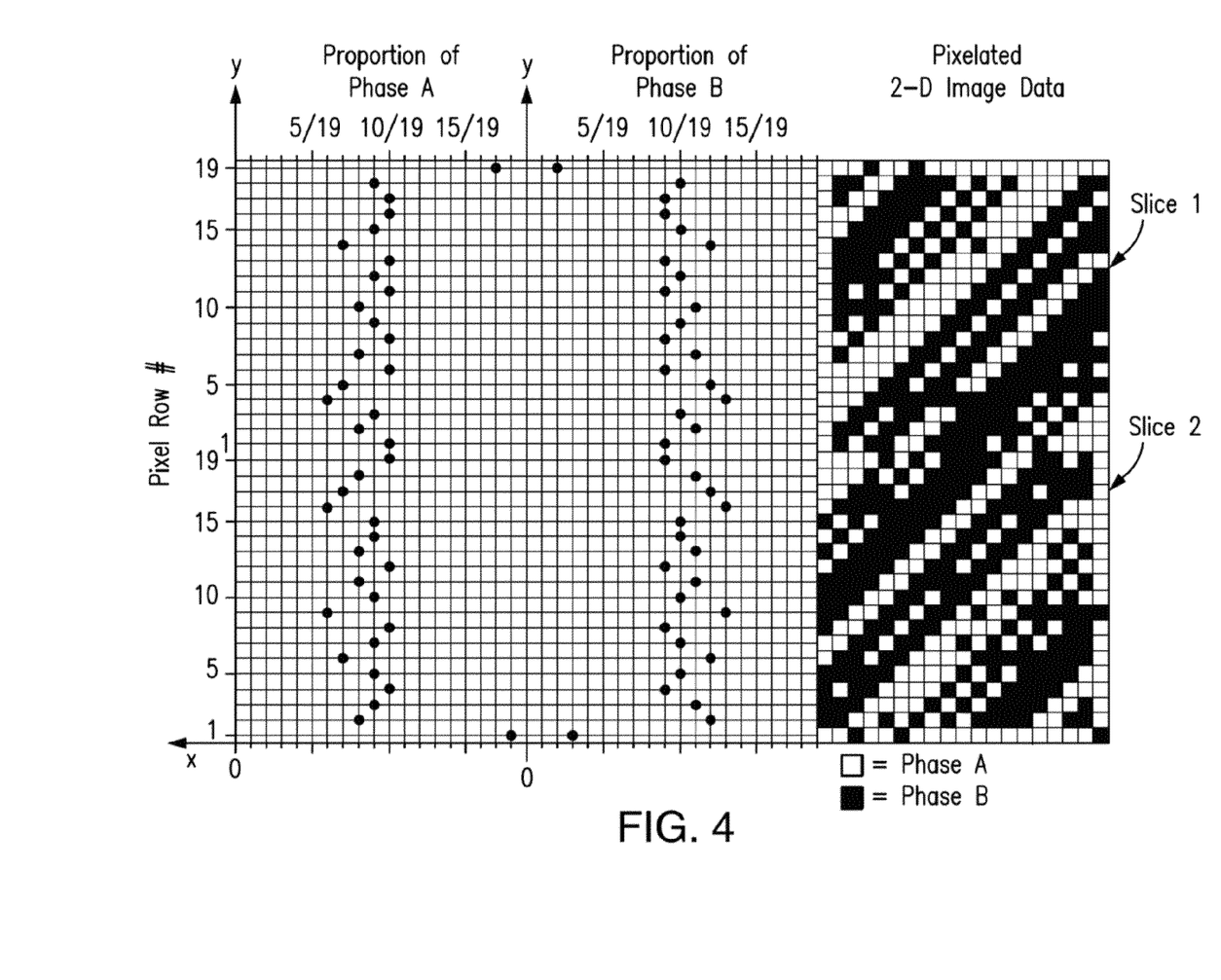
FIG. 4 shows two 2D segmented images of two sample slices in schematically enlarged depiction for sake of simplifying the illustration, wherein the images are stitched together as vertically adjacent graph portions in log form including laterally adjacent plots of the pore and kerogen proportions of corresponding pixel rows in each of the adjacent images.

FIG. 4 schematically shows a reporting style of an option of the present invention. Two pixelated 2D images captured for two different planar slices of a geological sample are stitched together on the right side of the log. Two images are shown in FIG. 4 to simplify the illustration. The number of images stitched together in the present method is not necessarily limited and can be any plurality, for example, 2 or more, or 5 or more, or 10 or more, or 15 or more, or from 2 to 50, or from 3 to 40, or from 4 to 30, or from 5 to 25, or from 10 to 20, or other values. Pixels are shown in FIG. 4 in greatly exaggerated size to simplify this illustration. 19×19 grids are shown for each image of this illustration. The side dimension of the pixels in CT or SEM imaging, for example, usually can be much smaller, e.g., from about 1 nm to about 50 nm, or from about 3 nm to about 30 nm, or other sizes. The pixels usually are square, but may be other two-dimensional geometries, such as rectangular. A two-dimensional plot of the proportional magnitude of a Phase A in each of the pixels rows of each image is plotted at the left hand side of the stitched image. A two-dimensional plot of the proportional magnitude of a Phase B in each of the pixels rows of each image also is plotted at the left hand side of the stitched image. The phase A and Phase B two-dimensional plots are laterally adjacent to the left of the images in this illustration. The order of the two-dimensional plots and images can reversed, or the image can be placed intermediate two-dimensional plots of proportional magnitudes of different phases in pixel rows of that image. The pixel row number for each of the corresponding images of the stitched image is shown along the indicated y-coordinate axis. The y-coordinate axis extends vertically, with the well direction from the geological sample was extracted oriented towards to the top of the sheet. Moving downward through the images moves further down and away from the upper end of the well. The indicated x-coordinate axis is oriented perpendicular to the y-coordinate axis. The proportional magnitude of a Phase A or Phase B, as applicable, in each of the pixels rows of each image is plotted along a line extending parallel to the x-coordinate axis and away from the y-axis at a location corresponding adjacent the pixel row being plotted for that phase. The plotted proportions are plotted as single data points in this illustration, but it will be appreciated that the plotting can be done continuously from point-to-point within each two-dimensional plot. The log form product of this process can be graphically displayed, stored in memory, printed, or any combinations thereof. The log form product can be displayed, for example, on a LED display, LCD display, CRT display, HD display, plasma screen, or other displays, stored in memory, printed on rolls or sheets of paper, or any combinations of these.

Figure 5:
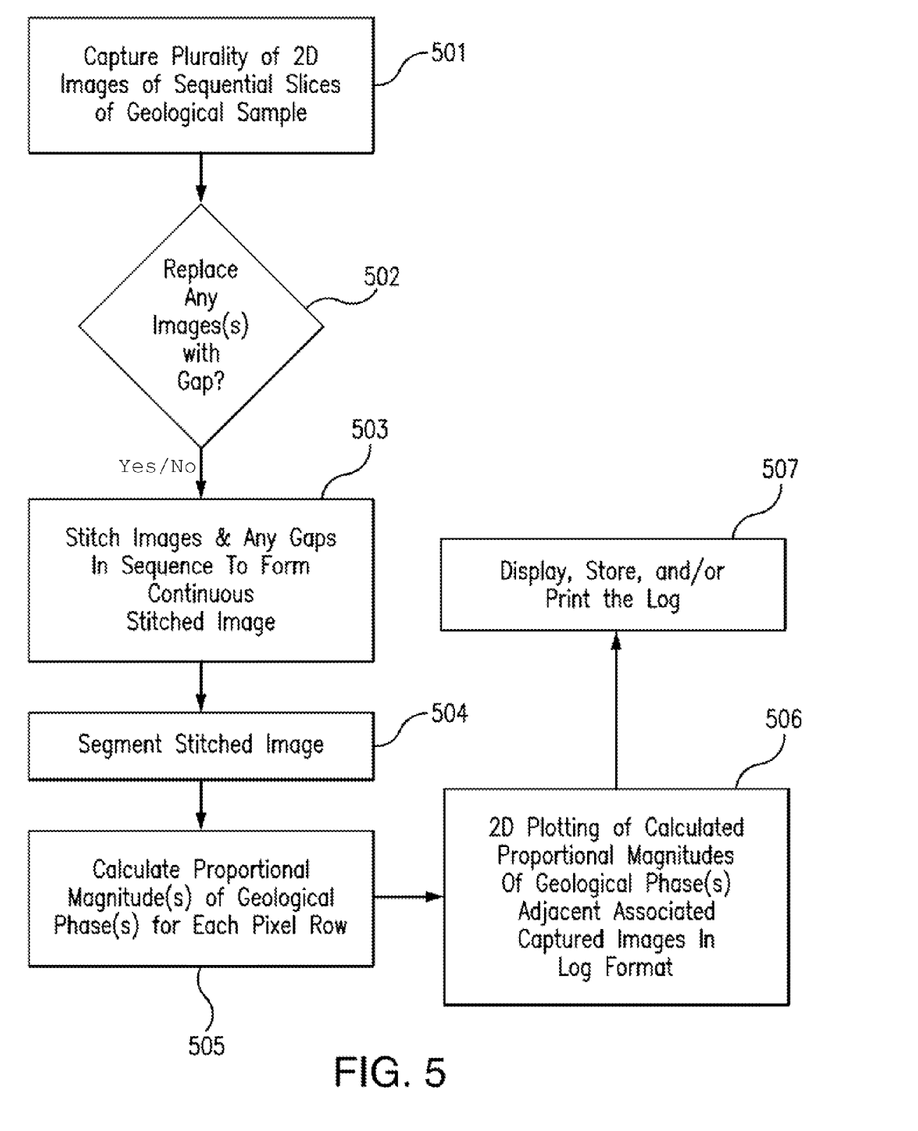
FIG. 5 is a process flow chart showing a method according to an example of the present application.

The process flow chart in FIG. 5 shows a method according to an example of the present application. In step 501, a plurality of 2D images which are captured of successive slices of a geological sample. As an option, the progression of captured images can be made in a sequence towards the interior of the sample. The direction of image capture could be reversed when a non-destructive image capture device is used. In step 502, once the images are captured, images can be removed from the acquired collection. For example, a captured image may include a geological anomaly or other consideration which, if retained, could skew the results. If removed, an image can be replaced with a gap in the log produced by the present method. In step 503, the captured images and any gaps are stitched in the sequence of capture to form a continuous stitched image. In step 504, the stitched image is segmented. In step 505, one or more proportional magnitudes of one or more geological phases are calculated for each pixel row of the stitched image. In step 506, the calculated proportional magnitudes of the one or more calculated geological phases are two-dimensionally plotted in a log format. As an option, the log format can include the two dimensional plots as presented laterally adjacent the associated captured images. In step 507, the log can be displayed, stored, printed, or any combinations thereof.

Figure 6:
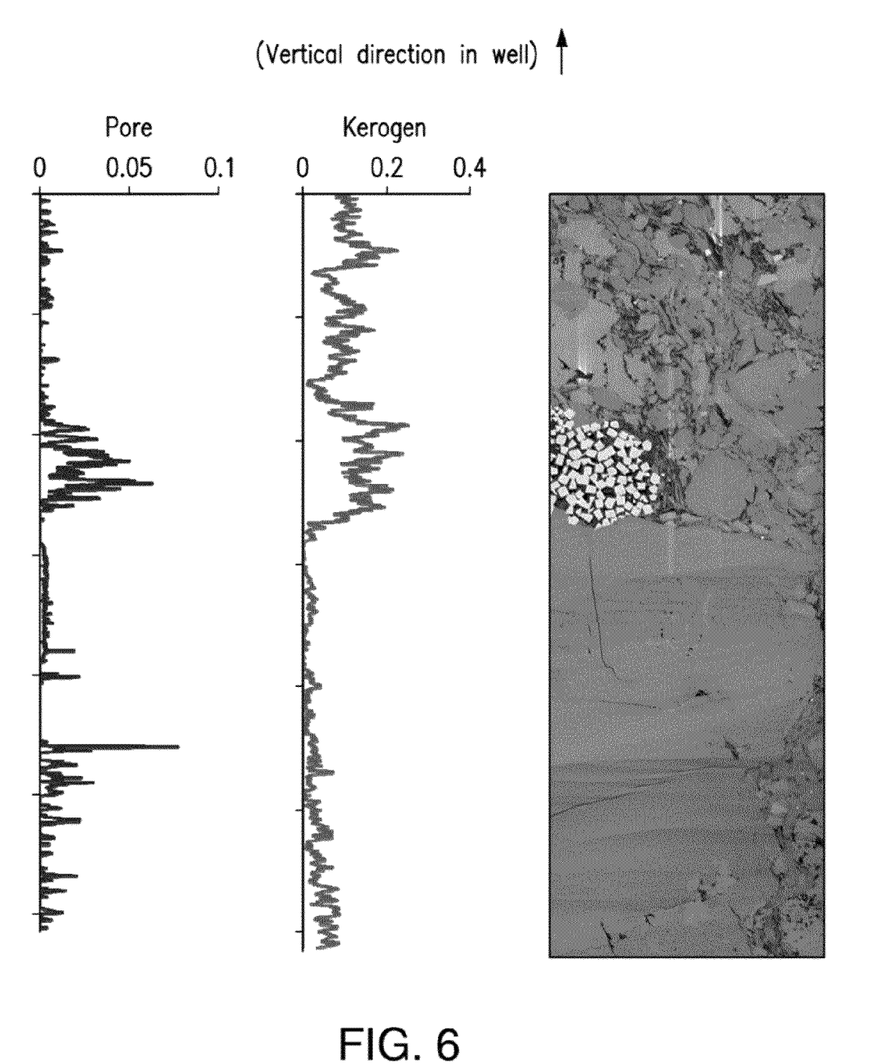
FIG. 6 shows two 2D segmented SEM images of two sample slices stitched together in vertically adjacent graph portions in log form including laterally adjacent plots of the pore and kerogen proportions of corresponding pixel rows in the associated adjacent images.

FIG. 6 shows two 2D segmented SEM images of two sample slices captured from a rock sample, which are stitched together in vertically adjacent graph portions in log form including laterally adjacent plots of the pore and kerogen proportions of corresponding pixel rows in the associated adjacent images. The two images shown are the above-indicated images 2D07 and 2D08. The vertical direction in the well is up in this log. Kerogen is a mixture of organic chemical compounds that make up a portion of the organic matter in some rocks, such as sedimentary rocks. Kerogen typically is insoluble in normal organic solvents because of the very large molecular weight (e.g., upwards of 1,000 Daltons) of its component compounds. When heated, some types of kerogen can release crude oil or natural gas.

Figure 7:
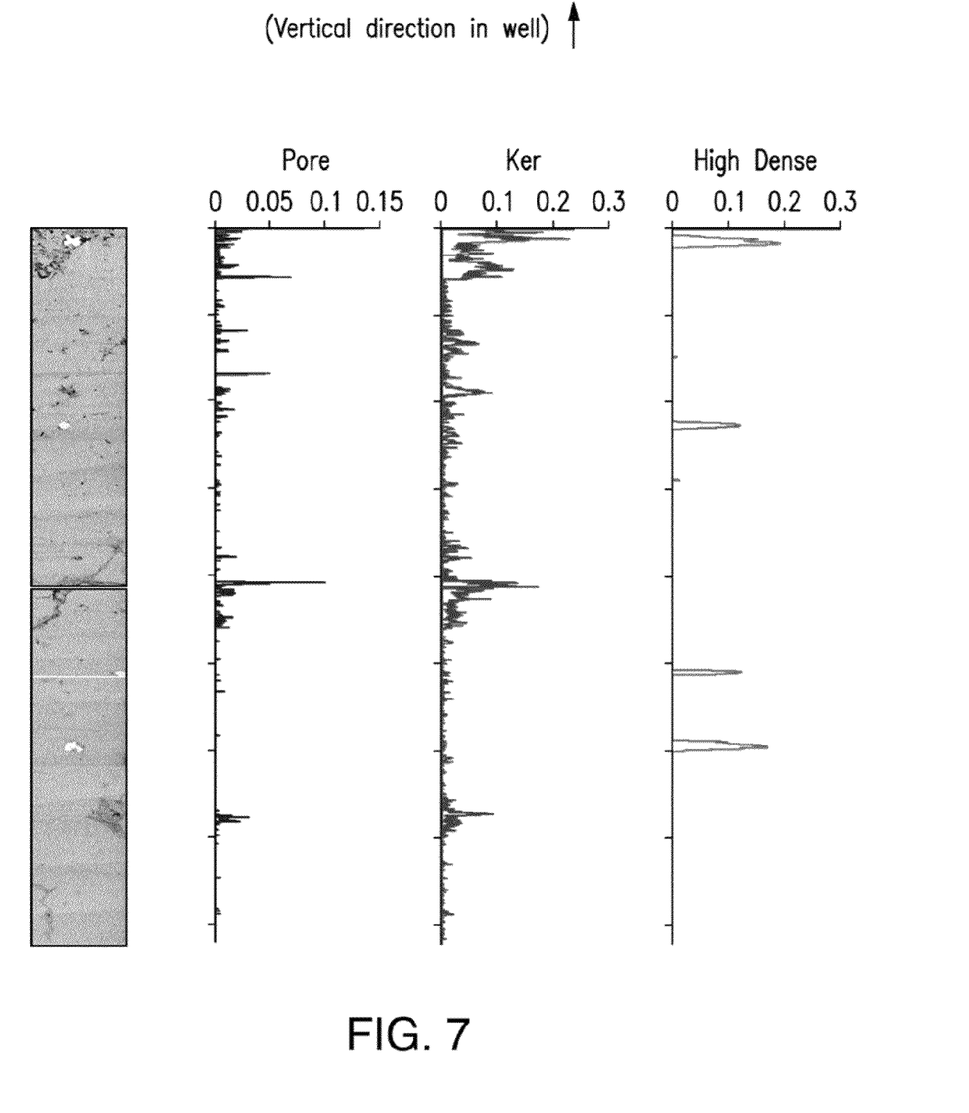
FIG. 7 shows eight 2D segmented SEM images of eight sample slices stitched together in vertically adjacent graph portions in log form including laterally adjacent plots of the pore, kerogen ("ker"), and high density mineral ("high dense") proportions of corresponding pixel rows in associated adjacent images.

FIG. 7 shows eight 2D segmented SEM images of eight sample slices captured from a rock sample, which are stitched together in vertically adjacent graph portions in log form including laterally adjacent plots of the pore, kerogen ("ker"), and high density mineral ("high dense") proportions of corresponding pixel rows in associated adjacent images. The rock sample was a shale rock. The vertical direction in the well is up in this log.

The present method can provide more intuitive results by maintaining reservoir orientation and can help in identifying key laminae for subsequent 3D analysis. The level of accuracy can be improved, as each 2D image can be characterized by many data points, for example, over 3,000 data points or more (one for each row of pixels), rather than just one. Using these log-like results can better highlight trends in geological samples, increasing analytical capability. The method may be used in upscaling 2D SEM data to other resolutions.

The techniques used to capture or acquire two-dimensional images for use in the method of the present invention are not necessarily limited. As an option, digital rock physics using digital computer tomographic (CT) and/or scanning electron microscope (SEM) images of rock samples can be used. The CT scanner uses X-rays and the SEM uses an electron beam for generation of two dimensional (2D) and/or three dimensional (3D) images of the drill cuttings, core samples, or other forms of samples retrieved from a geological formation. The images so generated can be in numerical form and their data content will be further explained below. After scanning, the samples can be saved for further analysis if a non-destructive scanning method is used, or may be discarded. In general, the instrument used to scan the core samples, or other types of retrieved samples from the formation (e.g., percussion samples, cuttings, etc.), can be selected based on how small are the pores in the rock and how much resolution is needed to produce a usable image.

The planar slice images can be obtained with non-destructive or destructive techniques on a geological sample using systems including tomographic scanning capability. As non-destructive techniques, examples of suitable CT scanners for making images usable with methods according to the invention, include, for example, tomographic x-ray transmission microscopes, such as Micro CT and Nano CT. For coarser samples, such as carbonates or sandstones, the Micro CT may provide sufficient resolution. When smaller pore samples, such as some shales, are tested, the higher Nano CT may be required. In addition, very dense rock formations, such as some shales, can require resolution beyond X-ray CT scanners. In these situations, scanning electron microscopes can be used instead. A destructive technique can include two-dimensional tomographic data acquisition and volume visualization through the application of serial FIB (Focused Ion Beam) sectioning that has recently emerged as a potential method to acquire, interrogate, and display multi-dimensional images for various substrate materials. For example, in U.S. Pat. Nos. 6,855,936 and 7,750,293 B2, systems have been provided which can be used for FIB-SEM (scanning electron microscope) tomographic methods. The FIB system can act like a nanoscale scalpel to remove very thin slices of material from a sample, while the SEM captures images of the sample's structure at each slice. The image output (images) generated by the CT, SEM, or FIB-SEM scanner, for example, can be transferred to a computer having program instructions for carrying out the indicated image analysis, plotting, and subsequent log formation/display.

For purposes herein, "segmentation" means a process of partitioning a digital image into multiple segments (sets of pixels). Image segmentation is typically used to locate objects and boundaries (lines, curves, etc.) in images. In segmentation of porous rock, for example, it can be used to allocate pore space and one or more non-porous phase regions and their boundaries. Image segmentation is the process of assigning a label to the pixels in an image such that pixels with the same label share certain visual characteristics. The result of image segmentation is a set of segments that collectively cover the entire image, or a set of contours extracted from the image. Each of the pixels in a region can be similar with respect to some characteristic or computed property, such as color, intensity, or texture. Adjacent regions are different with respect to the characteristic(s). General-purpose algorithms and techniques have been developed and used for image segmentation in the field of digital image processing. For example, a digital image of a rock sample can be segmented into its compositional classes. The term "compositional classes" can encompass, for example, open pores, mineral(s), optionally other types of materials, or any combinations thereof. Members of a single compositional class should possess the same composition and the same general structure relative to other compositional classes so that they influence to a similar extent the properties of the rock. As known in the field, there can be ambiguity in segmenting x-ray attenuation images (to use the X-ray microtomography example) into compositional classes of similar mineralogy because different rock minerals can have similar x-ray attenuations. Segmentation can be greatly aided if prior information about the mineral composition of the sample limits the number of possibilities for each pixel. As also known, where there is no prior information, x-ray diffraction can be used to determine mineralogy. If two compositional classes have equal or nearly equal x-ray attenuations, it may be necessary to use structural metrics to distinguish them as will be understood by those skilled in the art. These and other segmentation methods and techniques may be applied or adapted for use in a method and system of the present invention.

As an option, two-dimensional scanning electron microscope (SEM) images captured on rock sample can be cropped and segmented as part of a classification of pixels in the SEM images. As an option, the two-dimensional SEM images can be cropped and segmented to classify the pixels as pore, kerogen, mineral, or other similar or different classifications. The cropping, segmentation, and classification can be done, for example, with data visualization and analysis software adapted for use in the present methods. Standard modules of data visualization and analysis software can be used to process the arrays to do calculations for cropping the matrix. The screen menu options used for this purpose can vary. After cropping the matrix, the image can be segmented and pixels can be classified. Program modules can be programmed into data visualization and analysis software for executing this operation. The data visualization and analysis software-based segmentation package uses various image-processing techniques that include (a) noise reduction; (b) identifying the boundaries of the grains based on 3D surface gradients of the gray scale encountered in the original image; and (c) thresholding based on this image enhancement and focus sharpening.

The present invention also includes the following aspects/embodiments/features in any order and/or in any combination:

1. The present invention relates to a method of displaying geological image data, the method comprising:

(a) capturing a plurality of two-dimensional images of slices of a geological sample in a sequence, the plurality of two-dimensional images comprising a first dimensional direction and a second dimensional direction perpendicular to the first dimensional direction, wherein locations of at least one geological phase of the geological sample are captured;

(b) determining if any of the plurality of two-dimensional images in the sequence are to be replaced with a replacement gap when joined;

(c) joining the plurality of two-dimensional images and any gaps in the sequence to form a continuous stitched image;

(d) calculating proportional magnitudes of at least one geological phase based on the total geological phases for each of a plurality of adjoining rows of pixels in the stitched image, wherein the plurality of adjoining rows of pixels in the stitched image each extend from corresponding adjacent first positions along the first dimensional direction of the sequential slices in a direction parallel to the second dimensional direction of the sequential slices; and (e) plotting the proportional magnitudes calculated for the at least one geological phase for each of the plurality of adjoining rows of pixels in the stitched image at corresponding first adjacent locations on a first portion of a two-dimensional graph, wherein the two-dimensional graph comprises a first axis extending in a same direction as the first dimensional direction and a second axis extending in a same direction as the second dimensional direction, and the first adjacent locations on the first portion of the two-dimensional graph each comprise a first axis coordinate corresponding to the position of each row of the pixels and a second axis coordinate corresponding to the proportional magnitude for the corresponding row of pixels.

2. The method of any preceding or following embodiment/feature/aspect, further comprising displaying the two-dimensional graph parallel and adjacent to the captured images, wherein the plotting further comprising plotting of the proportional magnitudes adjacent the corresponding captured two-dimensional images in the stitched image.

3. The method of any preceding or following embodiment/feature/aspect, wherein each row of pixels in the images from which a proportional magnitude is calculated aligns with the plotting of that proportional magnitude on the two-dimensional graph.

4. The method of any preceding or following embodiment/feature/aspect, wherein steps (a) to (e) are applied to from about 10 to about 20 two-dimensional images.

5. The method of any preceding or following embodiment/feature/aspect, wherein the stitching comprising joining in a plane the plurality of images with each image positioned adjacent and below any preceding image of the sequence.

6. The method of any preceding or following embodiment/feature/aspect, wherein the images are displayed parallel to the graphed proportional magnitudes, such that a row of pixels from which a proportional magnitude is derived lines up with the plot of that proportional magnitude on the two-dimensional graph.

7. The method of any preceding or following embodiment/feature/aspect, wherein the stitched images are displayed vertically.

8. The method of any preceding or following embodiment/feature/aspect, wherein the two-dimensional images are two-dimensional scanning electron microscopic (SEM) images.

9. The method of any preceding or following embodiment/feature/aspect, wherein the capturing comprising segmenting the two-dimensional scanning electron microscope (SEM) images to classify pixels in the SEM images as pore, kerogen, or mineral.

10. The method of any preceding or following embodiment/feature/aspect, wherein the at least one geological phase comprises pore, kerogen, mineral, or a combination thereof.

11. The method of any preceding or following embodiment/feature/aspect, further comprising repeating steps (b), (c), (d), and (e) for at least one additional geological phase on a second two-dimensional graph.

12. The method of any preceding or following embodiment/feature/aspect, further comprising at least one of displaying the plottings, saving the plottings in a memory storage device, and printing the results.

13. A log produced by the method of any preceding or following embodiment/feature/aspect.

14. A method of displaying geological image data, the method comprising:

capturing a plurality of two-dimensional SEM images of sequential slices of a geological sample in a direction from a surface toward an interior of the geological sample, the plurality of two-dimensional images comprising a first dimensional direction and a second dimensional direction perpendicular to the first dimensional direction, wherein locations of at least one geological phase of the geological sample are captured;

determining if any of the plurality of two-dimensional images are to be replaced with a replacement gap when joined;

joining the plurality of two-dimensional SEM images and any gaps in sequence in a common plane with an image of a deeper slice joined below the image of an adjacent shallower slice to form a vertically stitched image having a vertical dimension and a horizontal dimension;

calculating a plurality of proportional magnitudes of a first geological phase based on the total geological phases for each of a plurality of adjoining rows of pixels in the vertically stitched image, wherein the plurality of adjoining rows of pixels in the vertically stitched image each extend from corresponding adjacent first positions along the first dimensional direction of the sequential slices in a direction parallel to the second dimensional direction of the sequential slices; and plotting the plurality of proportional magnitudes of the first geological phase for each of the plurality of adjoining rows of pixels of the first image at corresponding first adjacent locations on a first portion of a two-dimensional graph, wherein the two-dimensional graph comprises a first axis extending in a same direction as the first dimensional direction and a second axis extending in a same direction as the second dimensional direction, and the first adjacent locations on the first portion of the two-dimensional graph each comprise a first axis coordinate corresponding to the plurality of rows of adjacent pixels and a second axis coordinate corresponding to the plurality of proportional magnitudes.

15. The method of any preceding or following embodiment/feature/aspect, wherein the vertically stitched image is displayed parallel to the two-dimensional plot, such that a row of pixels of the vertically stitched image from which a proportional magnitude is derived lines up with the plot of that proportional magnitude on the two-dimensional graph.

16. The method of any preceding or following embodiment/feature/aspect, wherein the at least one geological feature comprises pore, kerogen, mineral, or a combination thereof.

17. The method of any preceding or following embodiment/feature/aspect, further comprising at least one of displaying the plottings, saving the plottings in a memory storage device, and printing the results.

18. The method of any preceding or following embodiment/feature/aspect, wherein the capturing comprising segmenting the two-dimensional SEM images to classify pixels in the SEM images as pore, kerogen, or mineral.

19. A two-dimensional plot in log form produced by the method of any preceding or following embodiment/feature/aspect.

20. A graphical display of geological image data comprising:

a vertically stitched image having a plurality of images of sequential planar slices of a geological sample joined in a plane with each image of a deeper slice joined below the image of an adjacent shallower slice, the vertically stitched image having a vertical direction and a horizontal direction; and a two-dimensional graph, comprising
a first axis and a second axis, and
a plurality of proportional magnitudes of at least one geological phase based on the total geological phases in the geological sample calculated from a plurality of adjoining vertical rows of pixels in the vertically stitched images; wherein the plurality of adjoining rows of pixels in the vertically stitched images each extend from corresponding adjacent first positions along the vertical direction of the first planar slice in a direction parallel to the horizontal direction of the first planar slice, the plurality of proportional magnitudes located at coordinates corresponding to respective positions on the first axis and calculated positions on the second axis corresponding to the plurality of proportional magnitudes, and the vertically stitched image is displayed parallel to the graphed plurality of proportional magnitudes, such that a row pixels of the stitched image from which the plurality of proportional magnitudes is calculated lines up respectively with the plots of the plurality of proportional magnitudes on the graph.

21. The graphical display of any preceding or following embodiment/feature/aspect, wherein:

the two-dimensional graph presents a plurality of proportional magnitudes of a first geological feature;

the graphical display further comprises at least one additional two-dimensional graph, having first and second axes, and presenting a plurality of proportional magnitudes of an additional geological feature, located at coordinates corresponding to respective positions on the first axis and calculated positions on the second axis corresponding to the plurality of proportional magnitudes of the additional geological feature;

the two-dimensional graph presenting the plurality of proportional magnitudes of the first geological feature is aligned with the at least one additional two-dimensional graph; and the respective positions along the first axis of the two-dimensional graph are aligned with the same positions along the first axis of the at least one additional two-dimensional graph.

22. The graphical display of any preceding or following embodiment/feature/aspect, wherein the at least one geological feature comprises pore, kerogen, mineral, or a combination thereof.

23. The graphical display of any preceding or following embodiment/feature/aspect, wherein the at least one geological feature and the at least one additional geological feature are different.

24. The graphical display of any preceding or following embodiment/feature/aspect, wherein the plurality of images are two-dimensional scanning electron microscopic (SEM) images.

25. The graphical display of any preceding or following embodiment/feature/aspect, wherein the two-dimensional SEM images are segmented with pixels in the SEM images classified as pore, kerogen, or mineral.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A method of displaying geological image data, the method comprising:
   (a) capturing a plurality of two-dimensional images of different planar slices at different depths through a geological sample in a sequence, the plurality of two-dimensional images comprising a first dimensional direction and a second dimensional direction perpendicular to the first dimensional direction, wherein locations of at least one geological phase of the geological sample are captured;
   (b) determining if any of the plurality of two-dimensional images in the sequence are to be replaced with a replacement gap when joined;
   (c) joining the plurality of two-dimensional images and any gaps in the sequence to form a continuous stitched image, wherein the joining comprises joining in a plane the plurality of images with each image positioned adjacent and below any preceding image of the sequence;
   (d) calculating proportional magnitudes of at least one geological phase based on the total geological phases for each of a plurality of adjoining rows of pixels in the stitched image, wherein the at least one geological phase comprises pore, kerogen, mineral, or a combination thereof, and wherein the plurality of adjoining rows of pixels in the stitched image each extend from corresponding adjacent first positions along the first dimensional direction of the sequential slices in a direction parallel to the second dimensional direction of the sequential slices; and
   (e) plotting the proportional magnitudes calculated for the at least one geological phase for each of the plurality of adjoining rows of pixels in the stitched image at corresponding first adjacent locations on a first portion of a two-dimensional graph, wherein the two-dimensional graph comprises a first axis extending in a same direction as the first dimensional direction and a second axis extending in a same direction as the second dimensional direction, and the first adjacent locations on the first portion of the two-dimensional graph each comprise a first axis coordinate corresponding to the position of each row of the pixels and a second axis coordinate corresponding to the proportional magnitude for the corresponding row of pixels.

2. The method of claim 1, further comprising displaying the two-dimensional graph parallel and adjacent to the captured images, wherein the plotting further comprising plotting of the proportional magnitudes adjacent the corresponding captured two-dimensional images in the stitched image.

3. The method of claim 2, wherein each row of pixels in the images from which a proportional magnitude is calculated aligns with the plotting of that proportional magnitude on the two-dimensional graph.

4. The method of claim 2, wherein the two-dimensional images are two-dimensional scanning electron microscopic (SEM) images.

5. The method of claim 4, wherein the capturing comprises segmenting the two-dimensional SEM images to classify pixels in the SEM images as pore, kerogen, or mineral.

6. The method of claim 1, wherein steps (a) to (e) are applied to from about 10 to about 20 two-dimensional images.

7. The method of claim 1, wherein the images are displayed parallel to the graphed proportional magnitudes, such that a row of pixels from which a proportional magnitude is derived lines up with the plot of that proportional magnitude on the two-dimensional graph.

8. The method of claim 1, wherein the stitched images are displayed vertically.

9. The method of claim 1, further comprising repeating steps (b), (c), (d), and (e) for at least one additional geological phase on a second two-dimensional graph.

10. The method of claim 1, further comprising at least one of displaying the plottings, saving the plottings in a memory storage device, or printing the results.

11. The method of claim 1, wherein at least one of the two-dimensional images in the sequence is replaced with a replacement gap when the images are joined.

12. The method of claim 1, wherein the calculating proportional magnitudes comprises calculating proportional magnitude of pore based on the total geological phases for each of a plurality of adjoining rows of pixels in the stitched image, calculating proportional magnitude of kerogen based on the total geological phases for each of a plurality of adjoining rows of pixels in the stitched image, and calculating proportional magnitude of mineral based on the total geological phases for each of a plurality of adjoining rows of pixels in the stitched image; and the plotting the proportional magnitudes comprises plotting the proportional magnitudes calculated for the pores for each of the plurality of adjoining rows of pixels in the stitched image at corresponding first adjacent locations of a first adjacent two-dimensional graph, and plotting the proportional magnitudes calculated for the kerogen for each of the plurality of adjoining rows of pixels in the stitched image at corresponding second adjacent locations of a second adjacent two-dimensional graph.

13. The method of claim 12, further comprising plotting the proportional magnitudes calculated for the mineral for each of the plurality of adjoining rows of pixels in the stitched image at corresponding third adjacent locations of a third adjacent two-dimensional graph.

14. A method of displaying geological image data, the method comprising:
  capturing a plurality of two-dimensional SEM images of sequential slices at different depths through a geological sample in a direction from a surface toward an interior of the geological sample, the plurality of two-dimensional images comprising a first dimensional direction and a second dimensional direction perpendicular to the first dimensional direction, wherein locations of at least one geological phase of the geological sample are captured;
  determining if any of the plurality of two-dimensional images are to be replaced with a replacement gap when joined;
  joining the plurality of two-dimensional SEM images and any gaps in sequence in a common plane with an image of a deeper slice joined below the image of an adjacent shallower slice to form a vertically stitched image having a vertical dimension and a horizontal dimension;
  calculating a plurality of proportional magnitudes of at least a first geological phase based on the total geological phases for each of a plurality of adjoining rows of pixels in the vertically stitched image, wherein the first geological phase comprises pore, kerogen, or mineral, and wherein the plurality of adjoining rows of pixels in the vertically stitched image each extend from corresponding adjacent first positions along the first dimensional direction of the sequential slices in a direction parallel to the second dimensional direction of the sequential slices; and
  plotting the plurality of proportional magnitudes of the first geological phase for each of the plurality of adjoining rows of pixels of the first image at corresponding first adjacent locations on a first portion of a two-dimensional graph, wherein
    the two-dimensional graph comprises a first axis extending in a same direction as the first dimensional direction and a second axis extending in a same direction as the second dimensional direction, and
    the first adjacent locations on the first portion of the two-dimensional graph each comprise a first axis coordinate corresponding to the plurality of rows of adjacent pixels and a second axis coordinate corresponding to the plurality of proportional magnitudes.

15. The method of claim 14, wherein the vertically stitched image is displayed parallel to the two-dimensional plot, such that a row of pixels of the vertically stitched image from which a proportional magnitude is derived lines up with the plot of that proportional magnitude on the two-dimensional graph.

16. The method of claim 14, further comprising at least one of displaying the plottings, saving the plottings in a memory storage device, or printing the results.

17. The method of claim 14, wherein said capturing comprising segmenting the two-dimensional SEM images to classify pixels in the SEM images as pore, kerogen, or mineral.

* * * * *